(12) United States Patent
de Juan et al.

(10) Patent No.: US 12,164,095 B2
(45) Date of Patent: Dec. 10, 2024

(54) MINIMALLY-INVASIVE TOOLS AND METHODS FOR ACCESSING THE MIDDLE AND INNER EAR THROUGH THE TYMPANIC MEMBRANE

(71) Applicant: Spiral Therapeutics Inc., Brisbane, CA (US)

(72) Inventors: Eugene de Juan, Brisbane, CA (US); Signe Erickson, Brisbane, CA (US); Charles Limb, Brisbane, CA (US); Hugo Peris, Brisbane, CA (US); Nikhil Talreja, Brisbane, CA (US); Andrew Ayoob, Brisbane, CA (US)

(73) Assignee: Spiral Therapeutics Inc., South San Francisco, CA (US)

( * ) Notice: Subject to any disclaimer, the term of this patent is extended or adjusted under 35 U.S.C. 154(b) by 620 days.

(21) Appl. No.: 17/155,564

(22) Filed: Jan. 22, 2021

(65) Prior Publication Data

US 2021/0228849 A1 Jul. 29, 2021

Related U.S. Application Data

(60) Provisional application No. 63/082,996, filed on Sep. 24, 2020, provisional application No. 63/081,015, (Continued)

(51) Int. Cl.
*A61M 31/00* (2006.01)
*A61B 1/018* (2006.01)
(Continued)

(52) U.S. Cl.
CPC .......... *G02B 21/0012* (2013.01); *A61B 1/018* (2013.01); *A61B 1/227* (2013.01);
(Continued)

(58) Field of Classification Search
CPC ............ A61B 17/3468; A61B 17/3415; A61B 17/3205; A61B 17/3423; A61B 17/3478;
(Continued)

(56) References Cited

U.S. PATENT DOCUMENTS

| 4,335,713 A | 6/1982 | Komiya |
| 5,421,818 A | 6/1995 | Arenberg |

(Continued)

FOREIGN PATENT DOCUMENTS

| CN | 104703650 | 6/2015 |
| CN | 205964003 | 2/2017 |

(Continued)

OTHER PUBLICATIONS

PCT International Search Report and Written Opinion in International Appln. No. PCT/US2021/014561, dated Apr. 8, 2021, 9 pages.

(Continued)

*Primary Examiner* — Robert J Utama
*Assistant Examiner* — Justin L Zamory
(74) *Attorney, Agent, or Firm* — Fish & Richardson P.C.

(57) ABSTRACT

Intra-tympanic injections of therapeutics into the inner ear can be used to treat conditions such as hearing loss. One or more stabilizing devices that define working channels can be temporarily implanted in the tympanic membrane. Purpose-built instruments such as endoscopes, forceps, and injections instruments can be passed through the working channels of the stabilizer devices to access the inner ear where the therapy can be administered. Afterwards, the stabilizing devices can be removed from the tympanic membrane and the tympanic membrane can heal, typically without the need for sutures.

6 Claims, 10 Drawing Sheets

Related U.S. Application Data filed on Sep. 21, 2020, provisional application No. 63/080,510, filed on Sep. 18, 2020, provisional application No. 63/078,141, filed on Sep. 14, 2020, provisional application No. 63/077,448, filed on Sep. 11, 2020, provisional application No. 63/051,568, filed on Jul. 14, 2020, provisional application No. 63/040,495, filed on Jun. 17, 2020, provisional application No. 63/024,183, filed on May 13, 2020, provisional application No. 62/965,481, filed on Jan. 24, 2020.

(51) Int. Cl.
| | |
|---|---|
| A61B 1/227 | (2006.01) |
| A61B 17/29 | (2006.01) |
| A61B 17/32 | (2006.01) |
| A61B 17/3205 | (2006.01) |
| A61B 17/34 | (2006.01) |
| A61B 18/04 | (2006.01) |
| A61B 18/14 | (2006.01) |
| A61B 18/20 | (2006.01) |
| A61F 2/958 | (2013.01) |
| A61F 11/20 | (2022.01) |
| A61M 37/00 | (2006.01) |
| G02B 21/00 | (2006.01) |
| G02B 21/22 | (2006.01) |
| A61B 17/00 | (2006.01) |
| A61B 18/00 | (2006.01) |
| A61F 2/18 | (2006.01) |

(52) U.S. Cl.
CPC ...... *A61B 17/29* (2013.01); *A61B 17/320068* (2013.01); *A61B 17/3205* (2013.01); *A61B 17/3423* (2013.01); *A61B 17/3468* (2013.01); *A61B 17/3478* (2013.01); *A61B 18/04* (2013.01); *A61B 18/1485* (2013.01); *A61B 18/20* (2013.01); *A61F 2/958* (2013.01); *A61F 11/20* (2022.01); *A61F 11/202* (2022.01); *A61M 31/00* (2013.01); *A61M 31/002* (2013.01); *A61M 37/0015* (2013.01); *G02B 21/0032* (2013.01); *G02B 21/22* (2013.01); *A61B 2017/00115* (2013.01); *A61B 2017/00787* (2013.01); *A61B 2017/00867* (2013.01); *A61B 2017/32007* (2017.08); *A61B 2018/00327* (2013.01); *A61B 2217/005* (2013.01); *A61F 2002/183* (2013.01); *A61F 2250/0067* (2013.01); *A61M 2037/0023* (2013.01); *A61M 2037/0046* (2013.01); *A61M 2205/04* (2013.01); *A61M 2210/0662* (2013.01); *A61M 2210/0668* (2013.01)

(58) Field of Classification Search
CPC .. A61B 2017/3425; A61B 2017/00787; A61B 18/1485; A61B 2018/00327; A61F 11/00; A61F 11/202; A61F 2002/183; A61M 31/002; A61M 2210/0662
See application file for complete search history.

(56) References Cited

U.S. PATENT DOCUMENTS

| | | | |
|---|---|---|---|
| 6,024,726 A | 2/2000 | Hill | |
| 6,045,528 A | 4/2000 | Arenberg et al. | |
| 6,120,484 A | 9/2000 | Silverstein | |
| 6,440,102 B1 | 8/2002 | Arenberg et al. | |
| 6,648,873 B2 | 11/2003 | Arenberg et al. | |
| 7,351,246 B2 | 4/2008 | Epley | |
| 7,704,259 B2 | 4/2010 | Kaplan et al. | |
| 8,197,461 B1 | 6/2012 | Arenberg et al. | |
| 9,352,084 B2 | 5/2016 | Decker et al. | |
| 9,616,207 B2 | 4/2017 | Verhoeven et al. | |
| 10,130,514 B2 | 11/2018 | Imran et al. | |
| 10,492,670 B1 | 12/2019 | Bendory et al. | |
| 2003/0220536 A1 | 11/2003 | Hissong | |
| 2004/0133099 A1 | 7/2004 | Dyer et al. | |
| 2004/0172005 A1 | 9/2004 | Arenberg et al. | |
| 2004/0263958 A1 | 12/2004 | Bihr et al. | |
| 2008/0051804 A1 | 2/2008 | Cottler et al. | |
| 2010/0106134 A1 | 4/2010 | Jolly et al. | |
| 2011/0224629 A1 | 9/2011 | Jolly et al. | |
| 2013/0060131 A1 | 3/2013 | Oghalai et al. | |
| 2013/0085476 A1 | 4/2013 | Imran | |
| 2013/0245569 A1 | 9/2013 | Jolly et al. | |
| 2015/0209074 A1 | 7/2015 | Payne | |
| 2015/0265824 A1* | 9/2015 | Lalwani | A61M 37/0015 |
| | | | 606/186 |
| 2015/0290040 A1* | 10/2015 | Vaughan | A61F 11/202 |
| | | | 606/109 |
| 2016/0346511 A1 | 12/2016 | Cohen et al. | |
| 2017/0172804 A1 | 6/2017 | Watanabe et al. | |
| 2018/0085258 A1 | 3/2018 | Andreas et al. | |
| 2019/0015254 A1 | 1/2019 | Bendory et al. | |
| 2019/0321610 A1 | 10/2019 | Goldfarb et al. | |
| 2019/0321611 A1 | 10/2019 | Sacherman et al. | |
| 2020/0094030 A1 | 3/2020 | Kim et al. | |

FOREIGN PATENT DOCUMENTS

| | | |
|---|---|---|
| WO | WO 1994010596 | 5/1994 |
| WO | WO 2019/066097 | 4/2019 |
| WO | WO 2019116024 | 6/2019 |
| WO | WO 2019/152866 | 8/2019 |
| WO | WO 2019200259 | 10/2019 |
| WO | WO 2020115674 | 6/2020 |

OTHER PUBLICATIONS

Extended European Search Report in European Appln No. 21744487.6, dated Dec. 20, 2023, 8 pages.

* cited by examiner

MINIMALLY-INVASIVE TOOLS AND METHODS FOR ACCESSING THE MIDDLE AND INNER EAR THROUGH THE TYMPANIC MEMBRANE

CROSS-REFERENCE TO RELATED APPLICATIONS

This application claims the benefit of priority to U.S. Provisional Application No. 62/965,481 filed on Jan. 24, 2020, U.S. Provisional Application No. 63/024,183 filed on May 13, 2020, U.S. Provisional Application No. 63/040,495 filed on Jun. 17, 2020, U.S. Provisional Application No. 63/051,568, filed on Jul. 14, 2020, U.S. Provisional Application No. 63/077,448 filed on Sep. 11, 2020, U.S. Provisional Application No. 63/078,141 filed on Sep. 14, 2020, U.S. Provisional Application No. 63/080,510 filed on Sep. 18, 2020, U.S. Provisional Application No. 63/081,015 filed on Sep. 21, 2020, and U.S. Provisional Application No. 63/082,996 filed on Sep. 24, 2020. The disclosures of the prior applications are hereby incorporated by reference in their entirety.

BACKGROUND

Hearing loss can be a result of a variety of ear disorders. Conductive Hearing Loss (CHL) involves the loss of normal mechanical pathways for sound to reach the hair cells in the cochlea, for example due to malformation, accumulation of fluid in the middle ear, presence of tumors, and/or damage to ossicles. SensoriNeural Hearing Loss (SNHL) is due to the absence of, or damage to, hair cells in the cochlea, or to the acoustic nerve. SNHL is typically associated with exposure to loud noise, head trauma, aging, infection, Meniere's Disease, tumors, ototoxicity, and the like.

Therapeutic treatments of hearing loss are known. The need exists for safe, direct, and effective drug delivery devices and methods capable of providing therapeutic effect in treating hearing loss and other maladies of the ear, in particular, the middle and inner ear.

BRIEF DESCRIPTION OF THE DRAWINGS

These and other aspects will now be described in detail with reference to the following drawings. Generally speaking the figures are not to scale in absolute terms or comparatively but are intended to be illustrative. Also, relative placement of features and elements may be modified for the purpose of illustrative clarity.

DETAILED DESCRIPTION

Figure 1:
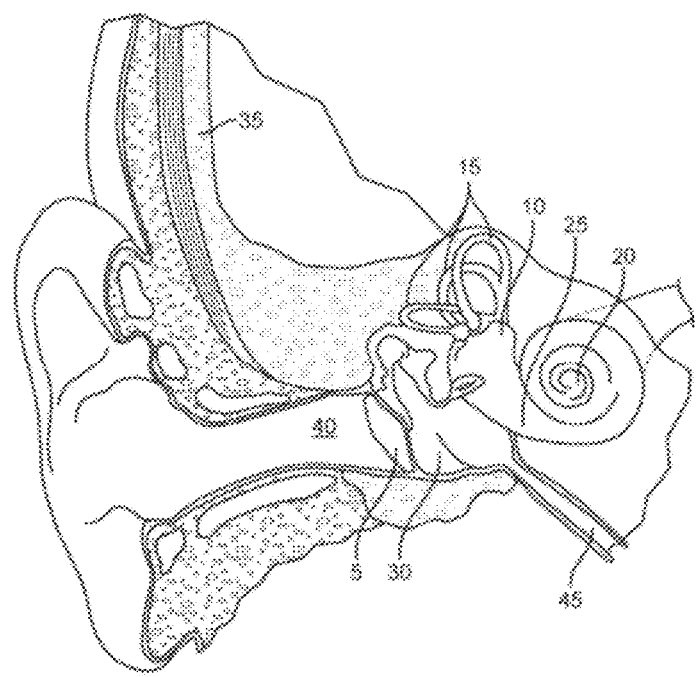
FIG. 1 illustrates the anatomy of an ear in coronal section view.

Conductive Hearing Loss (CHL) involves the loss of normal mechanical pathways for sound to reach the hair cells in the cochlea, for example due to malformation, accumulation of fluid in the middle ear, presence of tumors, and/or damage to ossicles. SensoriNeural Hearing Loss (SNHL) is due to the absence of, or damage to, hair cells in the cochlea, or to the acoustic nerve. SNHL is typically associated with exposure to loud noise, head trauma, aging, infection, Meniere's Disease, tumors, ototoxicity, and genetic diseases like Usher's disease, and the like.

Treatment of SNHL depending on the cause can include drug treatments for hair cell and cochlear nerve afferents regeneration, reversal of cochlear oxidative stress damage, and apoptosis inhibition and reversal of inflammation. There are several drugs in the final stages of clinical development for the treatment of hearing loss including STS (Fennec Pharmaceuticals) to protect against cisplatin-induced hearing loss; AM-101 (Auris Medical) for the treatment of tinnitus; AM-111 (Auris Medical) for otoprotection in acute inner ear hearing loss; OTO-104 (Otonomy) for the treatment of Meniere's Disease; SPI-1005 (Sound Pharmaceuticals) for the treatment of mild to moderate acute noise-induced hearing loss and for the treatment of Meniere's Disease.

The inner ear is difficult to treat effectively. For example, the inner ear accounts for only 0.004% of the average circulating blood volume and is encapsulated in one of the densest bones in the body. These, combined with the presence of the blood-labyrinth barrier (BLB), limit access of most therapeutic agents to the inner ear. Oral, intravenous, and intramuscular routes of administration are inefficient and require high doses and the risk of systemic side effects. Local drug delivery methods are also known. For example, inner ear therapeutics (e.g. drugs formulated as biocompatible gels) can be delivered via intra-tympanic injections into the middle ear across the tympanic membrane (TM). Passive diffusion of agents from the middle ear to the inner ear following intra-tympanic injection has variable efficacy due to anatomical variations, such as the presence of pseudomembrane covering the round window membrane, failure of the injected formulation to contact the round window membrane and limited permeability of the round window and oval window membranes. Further, rapid clearance of agents from the perilymph of the inner ear results in the need for repeated intra-tympanic injections, which are undesirable for patients and are associated with cumulative risk of infection, inflammation, and long-term damage to the tympanic membrane, in addition to the risk of lower compliance. Accurate placement of formulations in proximity to the round window membrane and assessment and removal of pseudo membrane structures would greatly improve effectiveness of therapy, but cannot be readily achieved with current intra-tympanic procedures, which are performed "blindly" without visualization of middle ear structures.

Direct delivery of therapeutics into the inner ear can also be achieved by injecting agents or drug releasing implants directly into the inner ear either through the round window membrane or by drilling a small cochleostomy. This procedure would be analogous to the placement of implants for cochlear stimulation. However, such procedures are currently performed in a relatively invasive manner, by creating a post auricular incision and drilling through the mastoid bone to the middle ear cavity. The degree of invasiveness of the current middle and inner ear procedures is too high to justify the precise delivery of therapeutics into the inner ear for the purpose of clinical trials and for their subsequent adoption as valuable treatments for inner ear disorders. A less invasive approach is needed.

The systems described here provide a more effective administration of inner ear therapeutics, whether via intratympanic administration or intracochlear administration, by providing minimally invasively access to the middle ear through the ear canal and tympanic membrane. The systems described herein also improve accessibility for various otological surgical procedures, such as cholesteatoma removal, tympanic membrane repair and ossicular chain repair, and allow them to be performed in a less invasive manner.

The materials, compounds, compositions, articles, and methods described herein may be understood more readily by reference to the following detailed description of specific aspects of the disclosed subject matter and the Examples included therein. Before the present materials, compounds, compositions, articles, devices, and methods are disclosed and described, it is to be understood that the aspects described below are not limited to specific methods or specific reagents, as such may vary. It is also to be understood that the terminology used herein is for the purpose of describing particular aspects only and is not intended to be limiting.

Unless defined otherwise, all technical and scientific terms used herein have the same meaning as is commonly understood by one of skill in the art to which the invention(s) belong. All patents, patent applications, published applications and publications, websites and other published materials referred to throughout the entire disclosure herein, unless noted otherwise, are incorporated by reference in their entirety. In the event that there are pluralities of definitions for terms herein, those in this section prevail. Where reference is made to a URL or other such identifier or address, it is understood that such identifiers can change and particular information on the internet can come and go, but equivalent information is known and can be readily accessed, such as by searching the internet and/or appropriate databases. Reference thereto evidences the availability and public dissemination of such information.

As used herein, relative directional terms such as anterior, posterior, proximal, distal, lateral, medial, sagittal, coronal, transverse, etc. are used throughout this disclosure. Such terminology is for purposes of describing devices and features of the devices and is not intended to be limited. For example, as used herein "proximal" generally means closest to a user implanting a device and farthest from the target location of implantation, while "distal" means farthest from the user implanting a device in a patient and closest to the target location of implantation.

As used herein, a disease or disorder refers to a pathological condition in an organism resulting from, for example, infection or genetic defect, and characterized by identifiable symptoms.

As used herein, treatment means any manner in which the symptoms of a condition, disorder or disease are ameliorated or otherwise beneficially altered. Treatment also encompasses any surgical or pharmaceutical use of the devices described and provided herein.

As used herein, amelioration or alleviation of the symptoms of a particular disorder, such as by administration of a particular pharmaceutical composition, refers to any lessening, whether permanent or temporary, lasting, or transient that can be attributed to or associated with administration of the composition.

As used herein, an effective amount of a compound for treating a particular disease is an amount that is sufficient to ameliorate, or in some manner reduce the symptoms associated with the disease. Such an amount can be administered as a single dosage or can be administered according to a regimen, whereby it is effective. The amount can cure the disease but, typically, is administered in order to ameliorate the symptoms of the disease. Repeated administration can be required to achieve the desired amelioration of symptoms. Pharmaceutically effective amount, therapeutically effective amount, biologically effective amount and therapeutic amount are used interchangeably herein to refer to an amount of a therapeutic that is sufficient to achieve a desired result, i.e. Therapeutic effect, whether quantitative or qualitative. In particular, a pharmaceutically effective amount, in vivo, is that amount that results in the reduction, delay, or elimination of undesirable effects (such as pathological, clinical, biochemical and the like) in the subject.

As used herein, sustained release encompasses release of effective amounts of an active ingredient of a therapeutic agent for an extended period of time. The sustained release may encompass first order release of the active ingredient, zero order release of the active ingredient, or other kinetics of release such as intermediate to zero order and first order, or combinations thereof. The sustained release may encompass controlled release of the therapeutic agent via passive molecular diffusion driven by a concentration gradient across a porous structure.

As used herein, a subject includes any animal for whom diagnosis, screening, monitoring or treatment is contemplated. Animals include mammals such as primates and domesticated animals. An exemplary primate is human. A patient refers to a subject such as a mammal, primate, human, or livestock subject afflicted with a disease condition or for which a disease condition is to be determined or risk of a disease condition is to be determined.

As used herein, a therapeutic agent referred to with a trade name encompasses one or more of the formulation of the therapeutic agent commercially available under the tradename, the active ingredient of the commercially available formulation, the generic name of the active ingredient, or the molecule comprising the active ingredient. As used herein, a therapeutic or therapeutic agents are agents that ameliorate the symptoms of a disease or disorder or ameliorate the disease or disorder. Therapeutic agent, therapeutic compound, therapeutic regimen, or chemotherapeutic include conventional drugs and drug therapies, including vaccines, which are known to those skilled in the art and described elsewhere herein. Therapeutic agents include, but are not limited to, moieties that are capable of controlled, sustained release into the body.

As used herein, a composition refers to any mixture. It can be a solution, a suspension, an emulsion, liquid, powder, a paste, aqueous, non-aqueous or any combination of such ingredients.

As used herein, fluid refers to any composition that can flow. Fluids thus encompass compositions that are in the form of semi-solids, pastes, solutions, aqueous mixtures, gels, lotions, creams and other such compositions.

As used herein, a kit is a packaged combination, optionally, including instructions for use of the combination and/or other reactions and components for such use.

Referring now to the figures, FIG. 1 shows the anatomy of an ear showing the outer ear, the middle ear, and the inner ear as well as a portion of the skull 35 and the Eustachian canal 45. The outer ear includes an auricle and an ear canal 40. The tympanic membrane 5 provides a barrier between the outer ear canal 40 and the middle ear or tympanic cavity 30. The inner ear can be divided into the bony labyrinth and the membranous labyrinth. The structural cavities within the bony labyrinth of the inner ear include the vestibule 10, the semicircular canals 15, and the cochlea 20. Hair cells of the cochlea 20 are critical in transducing acoustic signals into nerve impulses. The hair cells are bathed in secreted fluids such as perilymph supplied by cells that line the bony labyrinth and endolymph found within the membranous labyrinth, which help discern vibrations to assist in the process of hear as well as maintain a sense of balance and equilibrium. The round window 25 includes a round window membrane that in combination with the oval window of the cochlea 20 allow the fluid in the cochlea 20 to move.

Described herein are devices configured to directly access the middle ear cavities through the tympanic membrane in a sutureless, minimally-invasive manner. For example, the devices described herein provide direct access to the middle ear for the direct delivery of one or more therapeutic agent(s), implants, reservoirs, purpose-built instruments such as endoscopes, cutters, forceps, needles, aspiration devices, lasers, etc. to the inner ear or middle ear cavities. The direct access through the tympanic membrane is safer, less invasive, and requires no sealing or sutures of the tympanic membrane after removal of the devices.

The devices described herein can be a purely mechanical device or can be an at least partially powered instrument. In some implementations, as will be described in more detail below, the device incorporates one or more features that can provide stabilization, guidance, and/or visualization to a user allowing for greater control during the procedure and understanding of the relative location of the injection such that informed choices can be made on the fly.

Although the following describes tool and methodology in terms of surgical procedure through the tympanic membrane, it should be recognized that other surgical procedures can adapt the methodology to yield other types of sutureless surgical procedures in the ear. Any number of combinations of tools and/or agents can be delivered using any of the devices and systems described herein. Additionally, the surgical procedures include procedures performed on adults as well as pediatric applications.

Figure 4:
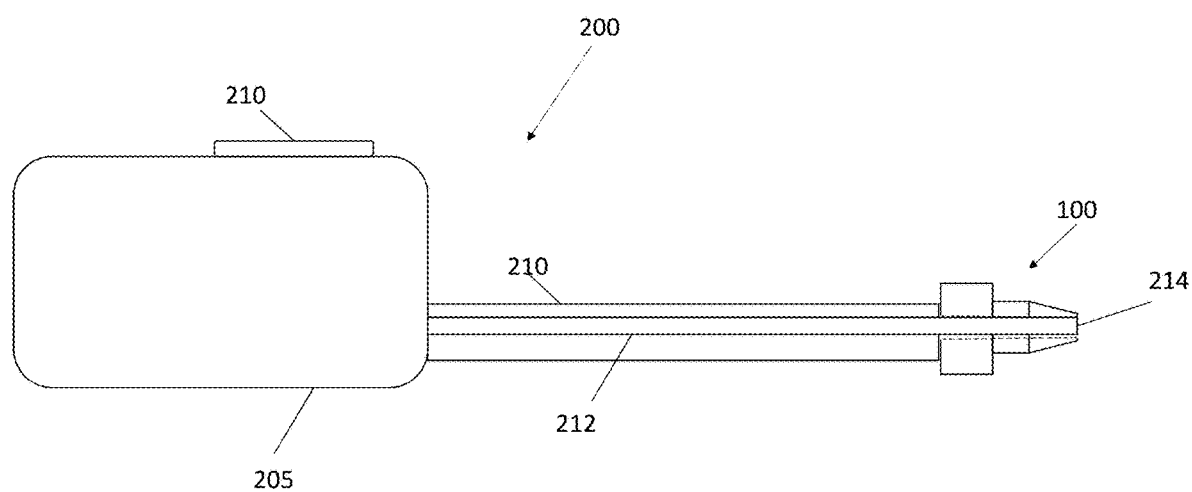
FIG. 4 illustrates the stabilizer device of FIG. 2 positioned on an insertion tool.

After preparing the ear for the surgical procedure, the surgical personnel generally mount the stabilizer device on a tool such as the insertion tool shown in schematic in FIG. 4. The stabilizer device can be inserted through the ear canal 40 and implanted in the tympanic membrane 5. This insertion procedure is repeated as needed to insert the number of stabilizer devices to meet the needs of a given procedure. In some implementations, the surgical procedure uses two surgical instruments simultaneously. Two stabilizer devices can be inserted to accommodate the two surgical instruments.

Figure 2:
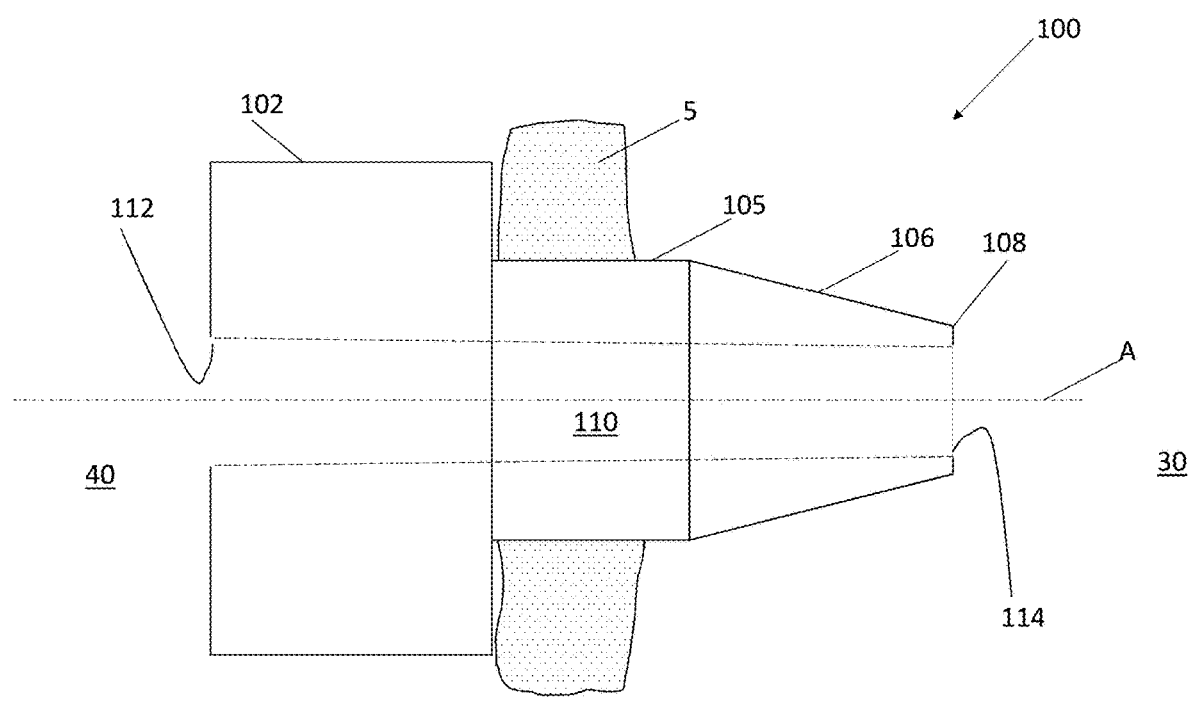
FIGS. 2 and 3 illustrate implementations of a stabilizer device positioned across the tympanic membrane.
Figure 3:
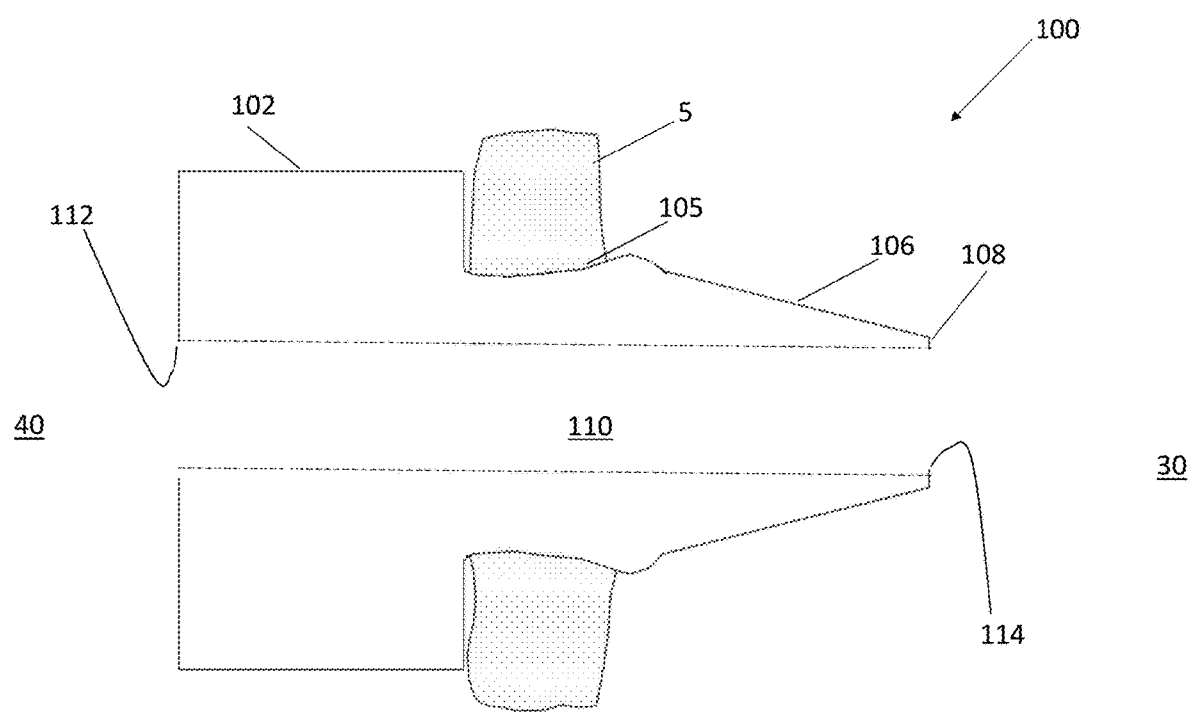

FIGS. 2 and 3 illustrate implementations of a stabilizer device 100 positioned within the tympanic membrane 5. The device 100 can include a proximal portion 102, a distal portion 106, and a transmembrane region 105 positioned between the proximal portion 102 and the distal portion 106. In some implementations, the transmembrane region 105 and distal portion 106 are configured to penetrate the tympanic membrane 5 whereas the proximal portion 102 is configured to stay external to the tympanic membrane 5.

The distal portion 106 is sized and shaped to pass through the tympanic membrane 5 in a minimally-invasive manner such that it is positioned within the middle ear distal of the tympanic membrane 5. The long axis of the distal portion 106 can be oriented to be approximately or substantially perpendicular to the external surface of the tympanic membrane 5 at the point of insertion. A distal end 108 of the distal portion 106 can be oriented so that the long axis is at any angle with respect to the tympanic membrane 5 and/or the longitudinal axis A of the device 100. The distal portion 106 is sized to have a width that is sufficiently small such that the removal of the distal portion 106 from the tympanic membrane 5 leaves an incision or fenestration that does not require sutures to heal. In some implementations, the largest diameter of the distal portion 106 is no greater than about 2 mm such that it can be inserted through a fenestration that is no greater than 3 mm in length.

The distal portion 106 can taper distally from a first outer diameter to a second, smaller outer diameter. In some implementations, the distal portion 106 tapers to the distal end 108. The distal end 108 can be sharpened to penetrate the tympanic membrane 5. For example, a force can be applied to the stabilizer device 100 during insertion to cause the distal end 108 to pierce the tympanic membrane 5 and pass through it without a prior fenestration being formed. The distal end 108 can form a non-traumatic tip that minimizes damage to the tissue being penetrated. The distal end 108 can incorporate any of a variety of non-coring bevel shapes of the needle art to facilitate insertion of the device 100 through the tympanic membrane 5. In other implementations, the distal portion 106 tapers to a smaller outer diameter distal end 108, but the distal end 108 is generally blunt. In this implementation, the stabilizer device 100 may be inserted through a pre-formed fenestration in the tympanic membrane 5. In other implementations, the device 100 can be preloaded onto an introducer tool with a sharpened tube or post element, such as a needle or knife, on the distal end that extends beyond portion 108 when in the loaded configuration. This sharpened element can create the fenestration and can be withdrawn after device 100 is in place, leaving the working channel 110 open in the final implanted configuration. Whether the distal end 108 is sharpened like a needle or generally blunt, the taper of the distal portion 106 allows for the stabilizer device 100 to pass smoothly through the tympanic membrane 5 to avoid catching on the membrane during distal advancement.

The proximal portion 102 is configured and sized to prevent over-insertion of the stabilizer device 100 through the tympanic membrane 5. For example, the proximal portion 102 can form a flange having an enlarged diameter compared to the distal portion 106 and the intervening transmembrane region 105. The angular arrangement of the proximal portion 102 relative to the long axis A of the device 100 can aid in preventing passage of the proximal portion 102 through the tympanic membrane 5. For example, the proximal portion 102 can extend approximately at a right angle relative to the long axis A of the device 100. The distal portion 106 of the stabilizer device 100 can be inserted through the tympanic membrane 5 until the tympanic membrane 5 is received within the transmembrane region 105 and the larger diameter proximal portion 102 abuts against an external surface of the tympanic membrane 5.

The proximal portion 102 can define a proximal opening 112 into a working channel 110 that extends through the stabilizer device 100 to a distal opening 114 at or near the distal end 108. The working channel 110 of the stabilizer device 100 may be a fully enclosed lumen extending from the proximal opening 112 in the proximal portion 102 to the distal opening 114 at or near the distal end 108. In other implementations, the working channel 110 can be a curved guiding surface (e.g., c-shaped) that is not fully enclosed, but is configured to receive the curved exterior surfaces of the instruments to guide the instrument through the tympanic membrane 5. The shape of the working channel 110 is configured to geometrically complement the shape of the surgical instruments being inserted through the device 100. The shape of the working channel 110 is generally cylindrical or arcuate. The size of the working channel 110 is configured to complement the size of the surgical instrument being inserted. In some implementations, the working channel 110 may have a cross-sectional diameter of about 25 gauge or 0.5 mm up to about 1.0 mm.

It should be appreciated that the overall length of the stabilizer device 100 can vary. In some implementations, the stabilizer device 100 is approximately 1.5 mm to about 3 mm long from proximal opening 112 to distal opening 114 and is formed of a relatively rigid material. In other implementations, the stabilizer device 100 is approximately 1.5 mm to about 5 mm long from proximal opening 112 to distal opening 114 and is formed of a relatively, flexible material that is similar to a flexible cannula. With each implementation, a smaller diameter transmembrane region extends about 0.1 mm to about 1.5 mm in length that is configured to traverse the tympanic membrane 5 and maintain positioning of the stabilizer device 100 within the membrane 5.

Distal portion 106 can dilate the incision in the tympanic membrane 5 as the device is inserted so that transmembrane region 105 is captured within the incision. The length of the distal portion 106 can be sufficient to allow for extension of the stabilizer device 100 into the middle ear such that the distal opening 114 is positioned a distance away from the internal surface of the tympanic membrane 5. However, the dimensions of distal portion 106 should be minimized so as avoid contact between the device and middle ear structures.

The proximal portion 102 can provide sufficient surface area and thickness to prevent the stabilizer device 100 from being pushed through the tympanic membrane 5 and to provide a sufficiently large surface area for surgical personnel to identify and locate the device 100 positioned within the tympanic membrane 5. The dimensions of the proximal portion 102 (e.g., outer diameter or thickness) can vary. In some implementations, the outer diameter of the proximal portion 102 can be between about 2 mm to about 5 mm. The proximal portion 102 can serve as a handle for the device 100 or the proximal portion 102 can additionally incorporate a grasping feature that is configured to be manipulated by a user for insertion and removal of the device from the ear. The grasping feature may be grasped with a tool such as a pair or forceps or by an insertion tool specifically configured to mate with the grasping feature.

The transmembrane region 105 can have an outer dimension relative to the proximal portion 102 that is sized and shaped to receive the tympanic membrane 5 when the distal portion 106 is inserted through the tympanic membrane 5. The transmembrane region 105 can have an outer diameter that is between 0.25 mm and 1.0 mm. The transmembrane region 105 can have a length along the long axis A of the stabilizer device 100 that is between about 0.10 and 0.5 mm. The outer diameter and length of the transmembrane region 105 is sufficient to receive the thickness of the tympanic membrane 5 while preventing buckling, tearing, or other forces from being imparted inadvertently on the membrane 5 upon insertion of the device 100. The outer diameter of the transmembrane region 105 can vary along its length. FIG. 2 illustrates an implementation of the stabilizer device 100 having a transmembrane region 105 that is substantially cylindrical such that the outer diameter remains relatively constant along its length. FIG. 3 illustrates an implementation of the stabilizer device 100 having a transmembrane region 105 that has a curved geometry along the longitudinal axis A of the device 100. In this implementation, the outer diameter enlarges towards the distal end before the distal portion 106 tapers towards the distal end 108 of the device 100. The outer diameter of at least a portion of the transmembrane region 105 can be larger than an outer diameter of the distal portion 106 at its proximal-most end (see FIG. 3).

The transmembrane region 105 can have a shape configured to aid in the retention of the device 100 within the tympanic membrane fenestration. The transmembrane region 105 can form an annulus or toroid. The cross-sectional profile of the transmembrane region 105 can be circular. The cross-sectional profile of the transmembrane region 105 can be elongated and sized to correspond to the shape of the fenestration through the tympanic membrane upon insertion of the device 100. For example, the fenestration can be a small incision that is slit shaped. The elongate cross-sectional profile of the transmembrane region 105 can improve the fit of the device 100 within this slit-shaped fenestration through the tympanic membrane 5. The elongated cross section may include a first dimension that is longer than a second dimension forming a dilated slit, dilated slot, lentoid, oval, ovoid, bi-convex, or elliptical shape.

The stabilizer device 100 can be formed of a material having a rigidity and strength to be inserted and removed from the tympanic membrane 5 while also withstanding stresses that may arise during manipulation of surgical instruments inserted therethrough. In some implementations, at least a portion of the stabilizer device 100 is formed of surgical metals such as stainless steel, titanium, platinum, Nitinol, and/or plastics such as polyimide, PEEK, fluoropolymers, silicone, and the like. In some implementations, the inserted portion of the device 100 can be formed of polyimide and have a maximum outer diameter of no more than about 20 gauge (8 mm). One or more portions of the stabilizer device 100 can be coated with or formed of a conformable material. For example, the retention feature 102 can be coated with or formed by over-molding with a material such as silicone or polyurethane.

The stabilizer device 100 can be an integral, one-piece structure such that the proximal portion 102, the transmembrane region 105 and the distal portion 106 are all part of the same structure. It should also be appreciated that one or more portions of the stabilizer device 100 can be separate components of the device 100 that are arranged to work with one another, but not necessarily rigidly affixed or integrated with one another. For example, the proximal portion 102 and the distal portion 106 can be removably coupled to one another.

The stabilizer device 100 is configured and sized so that its removal from the tympanic membrane 5 does not necessitate the use of sutures to seal the incision or fenestration formed in the tympanic membrane during insertion of the stabilizer device 100. Generally, a self-sealing fenestration through the tympanic membrane 5 is no greater than about 2 mm in length, preferably between about 0.5 mm and 1.5 mm in length. Although the tools and methods described herein provide the advantage of sutureless access to the middle and/or inner ear, this does not preclude a surgeon from applying one or more closure techniques upon removal of the stabilizer device 100. For example, if a surgeon so desires, one or more techniques for closure of the fenestration in the tympanic membrane 5 can be performed.

In use, a user may form one, two, or more fenestrations in the tympanic membrane 5. The fenestrations may be between about 0.25 mm and 1.25 mm in diameter. The fenestrations can be performed using an appropriate cutting tool such as a blade, a needle, a trephine, a laser, or other tool. A stabilizer device 100 may be implanted into each tympanic membrane fenestration. In some implementations, the fenestration is a slice through the tympanic membrane such as can be made with a needle. In other implementations, the fenestration is a hole in the tympanic membrane (e.g., made by a laser or trephine). The size of the stabilizer device positioned within the hole can be sized to fit that hole such that forces imparted on the instrument are distributed around a perimeter of the hole to prevent further tearing.

In some implementations, the cutting tool to form the fenestrations in the tympanic membrane 5 is the distal end 108 of the stabilizer device 100. In other implementations, the cutting tool is part of the tool used to insert the stabilizer device 100. For example, the stabilizer device 100 can be mounted on an insertion tool 200 (see FIG. 4). The insertion tool 200 can include a proximal handle 205 configured to be grasped by a user, one or more actuators 210 movable relative to the handle 205, a distal delivery shaft 210 projecting from the distal end of the handle 205, and a stylet 212. The stylet 212 can be inserted through the working channel 110 of the stabilizer device 100 such that the distal tip 214 of the stylet 212 extends beyond the distal opening 114 from the stabilizer device 100. The distal tip 214 of the stylet 212 can be beveled like a needle so it can be used to form the fenestration through the tympanic membrane 5. The actuator(s) 210 can be actuated to release the device 100 leaving it in position within the ear.

The handle 205, depending on whether the insertion tool 200 is intended to be durable or disposable, may be made of a high performance-engineering thermoplastic (e.g. PTFE) or of a metal such as stainless steel or aluminum. The handle 205 can be unitary, single-piece, molded construction or can be formed by two or more panels configured to couple together. The handle 205 can include threaded or friction fit panels configured to be opened to access an interior of the handle 205. The handle 205 may be similar in form factor to an otoscope, syringe, speculum, or other hand-held type instrument for use with the ear. The handle 205 can include an angular bend to ensure an unobstructed view through the operative microscope or one or more gripping features such as indentations or ergonomic features for gripping the tool 200.

As mentioned, the handle 205 can incorporate one or more actuators 210 such as one or more plungers, triggers, buttons, switches, keys, sliders, or combination thereof mounted on a portion of the handle 205 that are configured to be activated such as retracted, extended, pressed, squeezed, slid, or otherwise actuated to perform a certain function of the tool 200. The one or more actuators 210 can be incorporated into a portion of the handle 205 such as a hand-held portion in such a way that is ergonomically comfortable to a user.

The stabilizer device 100 may be provided as part of a kit that includes one or more stabilizer devices 100, an insertion tool 200, with or without the surgical instruments configured to be inserted through the stabilizer device 100.

Once the stabilizer device(s) 100 are positioned within the tympanic membrane 5, one or more instruments may be inserted through the working channel 110 of the device 100. The working channel 110 can provide a passage for introduction of any of a variety of instruments or fluids through the device 100. The instruments can be repeatedly inserted and removed through the working channel 110 without causing damage or strain on the tympanic membrane 5. Generally, the instruments inserted through the working channel 110 can have an outer diameter between 0.25 mm and 0.80 mm.

Any of a variety of instruments may be inserted through the working channel 110 including cutting instruments, infusing instruments, aspirating instruments, light transmitting instruments, energy applying instruments, tissue manipulating instruments, implant delivering instruments can be inserted through the working channel 110 of the stabilizer device 100. The instruments inserted through the working channel 110 of the one or more stabilizer device 100 can include small gauge endoscopes with, or without, a light source, and with, or without, a working channel. The instruments inserted through the working channel 110 of the one or more stabilizer device 100 can include a "chandelier" fiber-optic light source tailored for middle ear illumination. The small gauge chandelier fiber optic light source can provide hands-free endo-illumination directly into the middle ear and can reduce reflection off the tympanic membrane when viewed with transcanal illumination thereby improving visualization of middle ear structures. The instruments inserted through the working channel 110 of the one or more stabilizer device 100 can include micro-cutters/vertical scissors for pseudo membrane dissection. In some implementations, the cutting angle of the vertical scissors (i.e., angle of the blade relative to the shaft) can be between 45-120 degrees. The instruments inserted through the working channel 110 of the one or more stabilizer device 100 can include curved aspirating pick/forceps for pseudo membrane removal. The instruments inserted through the working channel 110 of the one or more stabilizer device 100 can include can be integrated with fiber optic components. In some implementations, a diffuse light source may be placed into the middle ear through the working channel 110 allowing for better trans-tympanic membrane visualization directly. This can provide endo-illumination of the features of interest and avoid problems associated with external illumination such as light reflection. Any of a variety of surgical interventions may be performed through the stabilizer devices 100 once implanted.

Small gauge endoscopes for visualization of the middle ear can be inserted through a less invasive tympanic membrane perforation. Endoscopes typically used in otology are about 3 mm in diameter. Smaller high-resolution wide-field endoscopes (e.g. 23 G) can be designed for the ear to enable visualization through small perforations in the tympanic membrane without creation of a surgical tympanomeatal flap.

In some implementations, the instruments inserted through the working channel 110 are configured to change shape and/or direction once exiting the distal opening 114 of the working channel 110. This allows for positioning the instruments, for example, at the round window membrane niche, for perforating, depositing material, and/or removing a false round window membrane niche. As an example, the instrument can be an extendable, articulable and/or curved microcannula for precise injections and/or placements of a drug formulation or implantable devices on, at, or through the RWM. Various other instruments are considered herein including a vented or small gauge needle that is curved, extendable, and/or articulable, ultrasharp knife for RWM perforation for controlled access to the inner ear cavity, diamond-dusted forceps and spatulas for improved gripping and scraping, as well as endolasers for RWM permeability enhancement.

The stabilizer device 100 provides for investigating middle ear disorders and for delivering therapeutics to treat inner ear disorders. For example, the stabilizer device 100 can be used to precisely place drug product at or near the oval window or RWM, remove any pseudo membrane or other mucosal obstruction that might inhibit absorption of drug product to the inner ear. The stabilizer device 100 can also provide for better visualization or and precise placement of implants or devices at or near the RWM, oval window, or other access points for the treatment of inner ear disorders.

After completion of the surgical procedure or administration of the therapy, the stabilizer device 100 is removed and the tympanic membrane 5 left to heal on its own without the need for additional intervention.

Figure 5:
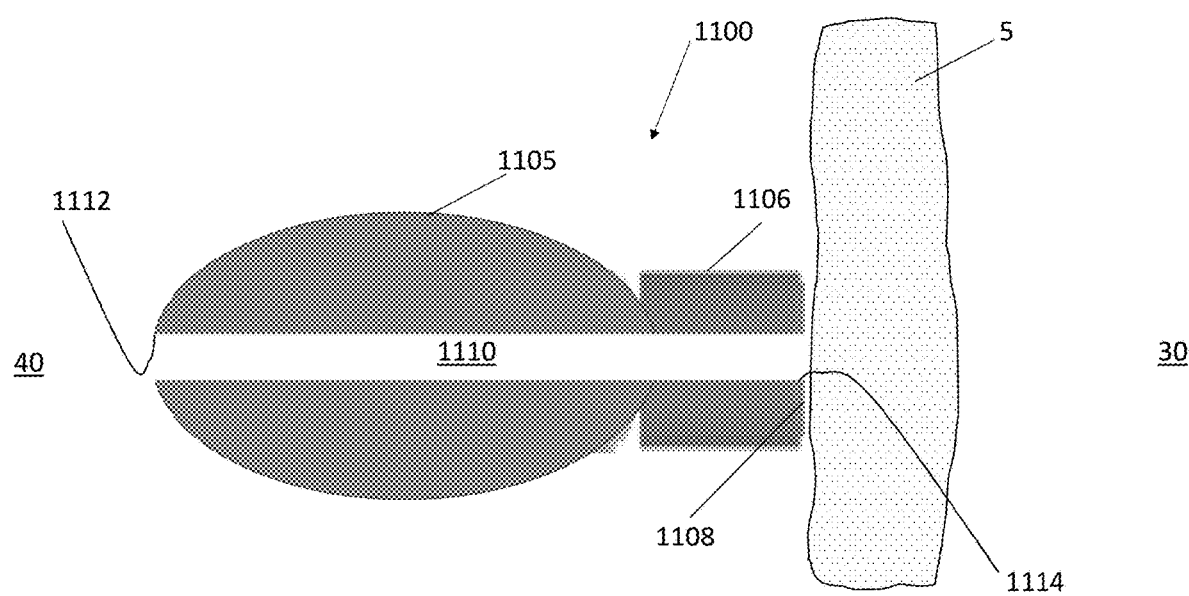
FIGS. 5 and 6 illustrate other implementations of a stabilizer device positioned external to the tympanic membrane.
Figure 6:
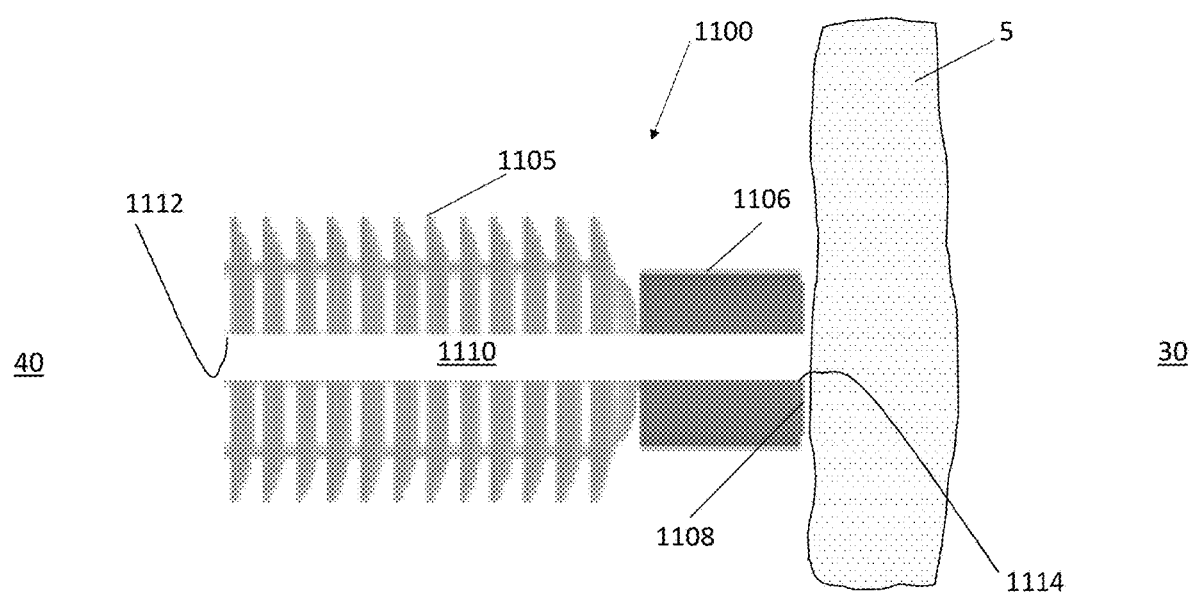

The tympanic membrane 5 is a delicate tissue that is prone to damage. However, direct contact with the membrane 5 can provide guidance for attaining proper instrument depth (e.g., during injections with a needle). FIGS. 5-6 illustrate an interrelated implementation of a stabilizer device 1100 that does not penetrate and is configured to remain fully external to the tympanic membrane 5 within the ear canal. The stabilizer device 1100 can include a proximal anchor 1105 that is configured to adjustably anchor against the ear canal 40 and that is coupled to a distal cannula 1106 configured to be positioned adjacent the external surface of the tympanic membrane 5. A working channel 1110 can extend through the device 1100 from a proximal opening 1112 to a distal opening 1114. The distal opening 1114 can be positioned at a distal end 1108 of the distal cannula 1106 for insertion of minimally-invasive instruments through the stabilizer device 1100 and through the tympanic membrane 5.

The proximal anchor 1105 can enlarge from an insertion configuration having a small outer diameter to a deployed configuration having a larger outer diameter configured to hold the device 1100 in place within the ear canal 40. The proximal anchor 1105 can safely engage the surrounding canal 40 with sufficient force and/or friction to inhibit movement of the stabilizer device 1100 or instruments inserted through the stabilizer device 1100 during treatment.

The configuration of the proximal anchor 1105 can vary including one or more rings, support legs, foam, balloon, expandable mesh, or other anchor. The proximal anchor 1105 can be conformal or compressible such that it deforms and takes on the shape of the ear canal 40 upon insertion. In some implementations, the proximal anchor 1105 can include an inner layer covered by an outer compressible layer. The outer compressible layer of the proximal anchor 1105 may include a compressible foam such as a urethane foam. Alternatively, the proximal anchor 1105 can be formed of a material such as gum rubber compounds, urethanes, fluorocarbon elastomer, butyl rubber, EPDM (Ethylene-Propylene Rubber), latex rubber, neoprene (polychloroprene), nitrile rubber (acrylonitrile), polybutadiene, silicone rubber, SBR (Stryrene-Butadiene Rubber), HNBR (Hydrogenated Nitrile Rubber), fluoroelastomer, fluorosilicone.

The proximal anchor 1105 may expand resiliently within the canal 40 or include soft solid elastomeric or plastically deformable polymers. The proximal anchor 1105 may also include an actively expanded feature such as a balloon, support rings, etc. FIG. 5 illustrates an implementation of the stabilizer device 1100 having an expandable balloon as the proximal anchor 1105. FIG. 6 illustrates an implementation of the stabilizer device 1100 having a plurality of support rings or flexible flanges configured to conform to the ear canal 40 upon insertion towards the tympanic membrane 5.

The proximal anchor 1105 can provide alignment within the ear canal 40 and direct the distal cannula 1106 toward the desired location of the tympanic membrane 5. The proximal anchor 1105 can be generally cylindrical having an outer diameter configured for smooth and comfortable insertion and engagement with the ear canal 40. The proximal anchor 1105 can allow for a slight seal to form between the ear canal wall and its outer surface. The length of the proximal anchor 1105 can vary. At least a portion of the proximal anchor 1105 can taper towards the distal cannula 1106, which can have a smaller outer diameter than a proximal end region of the proximal anchor 1105.

The working channel 1110 can have a uniform inner diameter as shown in FIGS. 5 and 6. The working channel 1110 also can have an inner diameter that varies along its length. For example, the working channel 1110 can be tapered with the smallest inner diameter near or at the distal opening 1114 and adjacent to the tympanic membrane 5. Such a configuration positions a fulcrum point of instruments extending through the working channel 1110 close in proximity to the tympanic membrane 5 and mitigates damage to the tympanic membrane 5 during manipulation and movements of the instruments.

In some implementations, the stabilizer device can incorporate a structure similar to tympanostomy tubes or a "grommet". As discussed above, the fenestration through the tympanic membrane that the stabilizer is placed into can be a hole made by a laser or trephine or a slice made by a surgical blade or needle. The size of the stabilizer device positioned within the hole can be sized to fit that hole such that forces imparted on the instrument are distributed around a perimeter of the hole to prevent further tearing. The grommet-like stabilizer device fitted into the hole made in the tympanic membrane can be left behind and allow for passage of the instruments in and out of the middle ear during a surgical procedure in a manner that distributes the instrument forces on the tympanic membrane thereby preventing tearing. In combination with the grommet-like stabilizer device or as a separate, stand-alone approach, a scaffold or fixation device (such as the proximal anchors described elsewhere herein) can be positioned within the ear canal allowing instrument forces to be directed towards the walls of the canal rather than solely by the tympanic membrane.

Figure 8A:
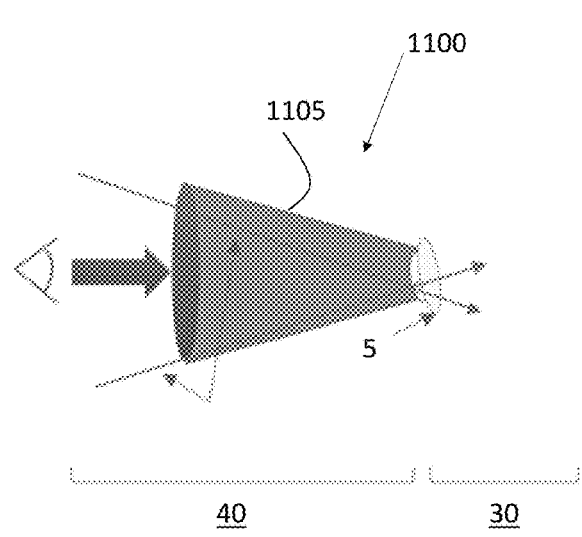
FIGS. 8A-8B illustrate another implementation of a stabilizer device positioned external to the tympanic membrane.
Figure 8B:
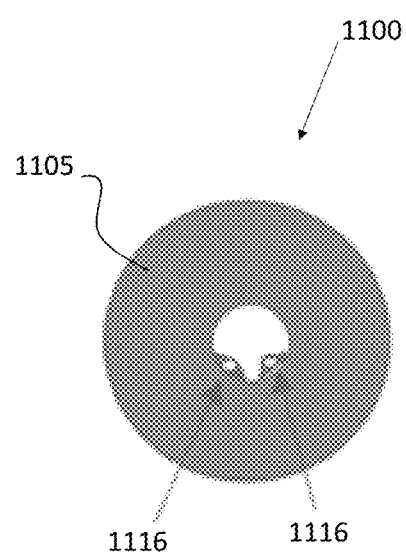

The configuration of this ear canal scaffold can vary as described herein. FIGS. 8A-8B show an implementation of a stabilizer device 1100 that includes a proximal anchor 1105 positioned within the ear canal 40 analogous to an otic speculum. The proximal anchor 1105 can further reduce forces that would otherwise be exerted on the tympanic membrane 5 during instrument manipulations, rotations, etc. The proximal anchor 1105 can be in the shape of a conical, adjustable speculum or cone fitted to the ear canal 40. The proximal anchor 1105 can be threaded or otherwise telescope to allow for adjustment in close proximity to the tympanic membrane 5. Instruments can be passed the interior of the proximal anchor 1105 and through one or more small rings 1116 (e.g., 0.5 mm to 1.0 mm in diameter) located on a distal face of the proximal anchor 1105 adjacent to the tympanic membrane 5 providing the fulcrum around which the instruments would rotate. The cone shape of the proximal anchor 1105 can define a larger inner viewing channel and the rings 1116 located at a distal end of the cone can provide smaller working channels through which one or more instruments may be inserted. The rings 1116 can provide stabilization and guidance for instrument manipulations as described elsewhere herein.

Figure 9:
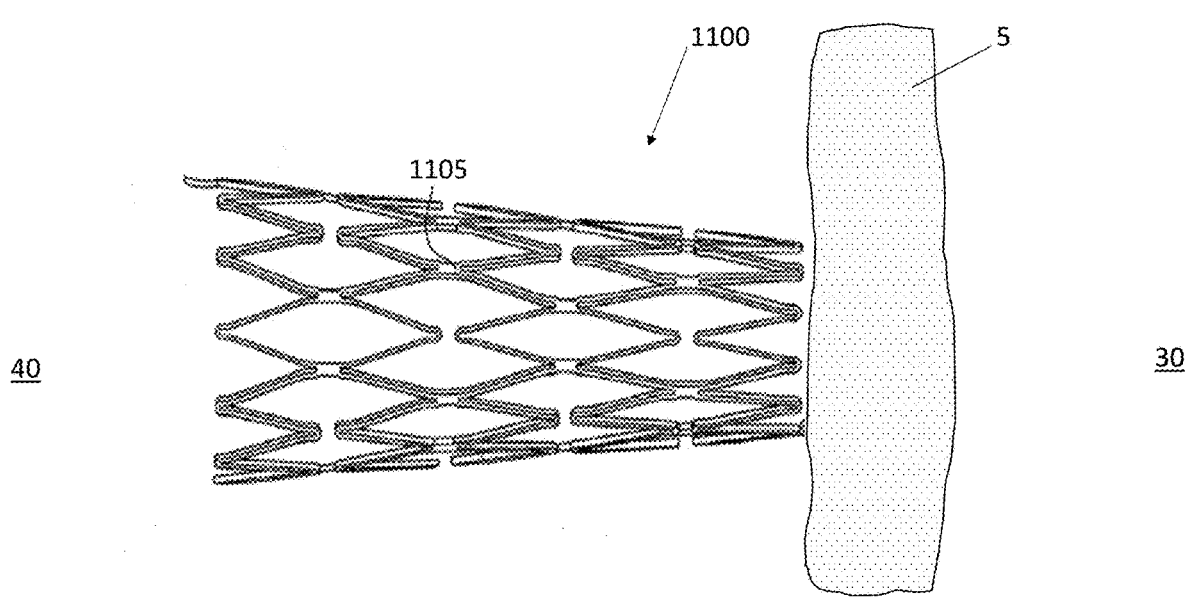
FIGS. 9-10 illustrate other implementations of a stabilizer device positioned external to the tympanic membrane.
Figure 10:
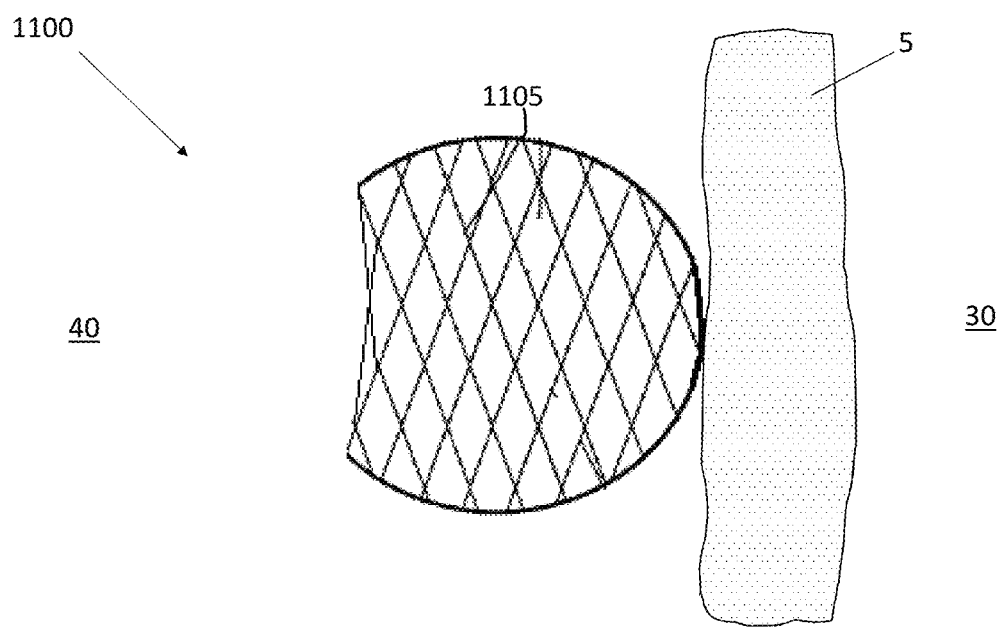

In some implementations, the proximal anchor 1105 can be an expandable mesh, braid, stent, basket, cage or other structural element configured to expand from a smaller dimension suitable for insertion to a larger dimension configured to fit within and anchor against the ear canal (see FIGS. 9-10). In some implementations, the proximal anchor 1105 can have a conical shape such that a central opening through the anchor 1105 provides access to the tympanic membrane as described above and as shown in FIG. 9. In other implementations, the proximal anchor 1105 can be closed at a distal end region near the tympanic membrane 5 (see FIG. 10). Openings in the mesh adjacent to the tympanic membrane 5 can be sized to allow passage of instruments. Fenestrations in the tympanic membrane 5 can be created after placement of the proximal anchor 1105 in order to ensure alignment of mesh openings for instrument passage into the middle ear 30. The proximal anchor 1105 can have any of a variety of shape. The proximal anchor 1105 can be basket-shaped or cup-shaped such that it is open on the proximal end to allow maximum instrument rotation around the distal mesh openings. Alternatively, the mesh openings can be of varying size, tapering from proximal to distal ends of the device. Following the end of the procedure, the proximal anchor 1105 can be collapsed and removed.

In some implementations, the stabilizer device 1100 can be similar in shape and form factor to an ear speculum. For example, the stabilizer device 1100 can include a sloped frustoconical shape and a smooth surface that permits insertion into the ear canal 40 to a limited depth without injuring the ear.

The working channel 1110 can extend through both the proximal anchor 1105 and the distal cannula 1106. The working channel 1110 can be sized to receive any of a variety of instruments as described above. The working channel 1110 can be coaxial with the longitudinal axis A of the device 1100 or can be offset from the axis A.

Figure 7A:
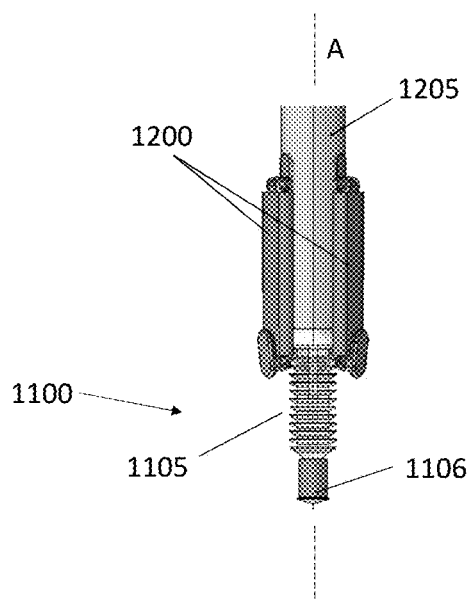
FIGS. 7A-7B illustrate stabilizer legs used in conjunction with the stabilizer device of FIG. 5 in a collapsed and expanded configuration, respectively.
Figure 7B:
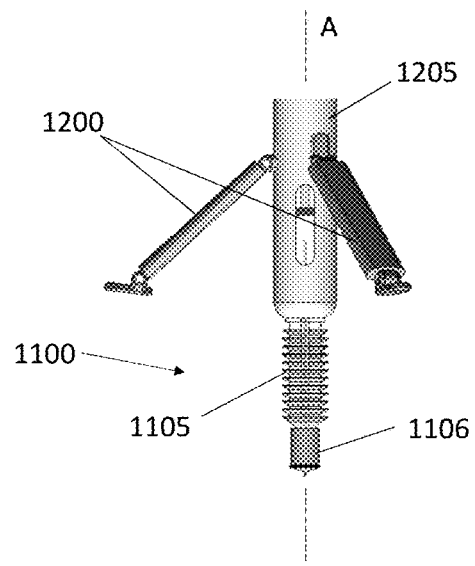

FIGS. 7A-7B show an implementation of a stabilizer device 1100 comprising a plurality of support legs 1200. The support legs 1200 can be expanded from an insertion configuration in which the support legs 1200 extend substantially parallel to the longitudinal axis A of the device 1100 to an enlarged configuration in which the support legs extend outward at an angle relative to the longitudinal axis A. The support legs 1200 can be coupled to a central housing 1205. In an implementation, the stabilizer device 1100 includes three collapsible legs 1200 coupled to a region of the central housing 1205 such that upon extension they form a tri-pod of stabilization relative to the distal cannula 1106. The legs 1200 can be arranged symmetrically around the longitudinal axis A of the device 1100. The legs 1200 can each extend outward by an angle relative to the axis A. The angle and also the length of the legs 1200 in the extended configuration allow for placement of the legs 1200 against a patient's ear canal 40. For example, a first leg 1200 can be positioned anteriorly on a patient's jaw, a second leg 1200 can be positioned caudally on a patient's skull near the neck, and a third leg 1200 can be positioned more cephalad on a patient's skull near the crown. Each leg 1200 can incorporate a foot member movable coupled to a distal end of the leg 1200 and configured to fold outward when the legs 1200 are in an extended configuration and fold inward when the legs 1200 are in a collapsed configuration. The legs 1200 can snap into the expanded configuration such that they avoid inadvertent collapse. The degree of extension of each leg 1200 can be selectable between a plurality of pre-set angles relative to the longitudinal axis A. Each foot member can swivel around its attachment with the leg 1200 between the inward and outward folded configurations to provide a tailored fit with the patient to provide better stabilization. In some implementations, the foot member is coupled to its leg 1200 by a barrel hinge type coupling having at least 2 degrees of freedom. In other implementations, the foot member is coupled to its leg 1200 by a ball and socket type coupling providing any degree of freedom. Any of the stabilizer devices described herein can be coupled to a plurality of support legs 1200.

The devices described herein can incorporate one or more features that aid in the visualization, aiming, and targeting of one or more instruments to prevent inadvertent penetrations and damage to delicate structures in the ear during a procedure. The devices described herein can be coupled to a viewing lens such as an otoscope lens or surgical microscope for the user to view the tympanic membrane 5 while the device is advanced toward the membrane. Endoscopes, video visualization devices, optical coherence tomography, ultrasound, and other viewing instruments or techniques, as well as one or more illumination elements, such as a LEDs, lenses, light pipes, filters, etc. that improve the visibility within the middle ear during use can be incorporated. Techniques to enhance viewing through the tympanic membrane directly using the operating microscope or otoscope, such as by applying glycerin or saline to the tympanic membrane to increase tympanic membrane transparency and reduce refractive index across the membrane in conjunction with middle ear illumination and/or wavelength filters can also be used to eliminate the need for an additional port for passage of an endoscope. Increasing membrane transparency and reducing variations in refractive index across the membrane, particularly when coupled with a middle ear light source, can allow visualization of the middle ear directly through the membrane via the operating microscope.

Direct trans-tympanic visualization can also be provided by infrared (IR) imaging or operative ocular coherence tomography (OCT). For example, a camera or probe directed at the tympanic membrane through the ear canal can provide visualization of the middle ear structures directly through an intact tympanic membrane.

Therapeutics and Diseases

The treatment devices described herein can be used to treat and/or prevent a variety of other conditions, including but not limited to hearing loss, including hidden hearing loss, noise-induced hearing loss, age-related hearing loss, drug-induced hearing loss, such as chemotherapy-induced hearing loss or aminoglycoside-induced hearing loss, sudden sensorineural hearing loss (SNHL), autoimmune inner ear disease, and the like. Any of a variety of ear disorders can be treated using the devices described herein. The treatment devices described herein can be used to treat other ear disorders such as tinnitus. The treatment devices described herein can be used to treat balance disorders including vertigo, Meniere's disease, vestibular neuronitis, vestibular schwannoma, labyrinthitis, and the like. The treatment devices described herein can be used to treat other ear disorders such as, otosclerosis, ossicular chain dislocation, cholesteatoma, middle ear infections, tympanic membrane perforations, and the like.

Examples of therapeutic agents that may be delivered from or with the help of the treatment devices described herein and/or are described in the applications incorporated by reference herein are provided below.

Therapeutics that can be delivered from or with the help of the treatment devices described herein include but are not limited to antioxidants, anti-inflammatoires, steroids, anti-microbials, NMDA receptor antagonists, nootropics, anti-apoptotic agents, neurotrophins, neuroprotective agents, neural protective proteins such as CNTF, BDNF, PEDF, NGF, and the like, cannabinoids, monoclonal antibodies, other proteins, gene therapy, iRNA, tyrosine kinase inhibitors (TKIs), dual leucine zipper kinase (DLK) inhibitors, and protein therapies like anti-VEGF.

As an example, the therapeutic agent can include, but is not limited to antimicrobials such as antibiotics such as tetracycline, chlortetracycline, bacitracin, neomycin, polymyxin, gramicidin, cephalexin, oxytetracycline, chloramphenicol kanamycin, rifampicin, ciprofloxacin, tobramycin, gentamycin, erythromycin and penicillin; antifungals such as amphotericin B and miconazole; anti-bacterials such as sulfonamides, sulfadiazine, sulfacetamide, sulfamethizole and sulfisoxazole, nitrofurazone and sodium propionate; antivirals such as idoxuridine, trifluorotymidine, acyclovir, ganciclovir and interferon; antiallergenics such as sodium cromoglycate, antazoline, methapyriline, chlorpheniramine, pyrilamine, cetirizine and prophenpyridamine; anti-inflammatoires such as hydrocortisone, hydrocortisone acetate, dexamethasone, dexamethasone 21-phosphate, fluocinolone, medrysone, prednisolone, prednisolone 21-phosphate, prednisolone acetate, fluorometholone, betamethasone, and triamcinolone; non-steroidal anti-inflammatoires such as salicylate, indomethacin, ibuprofen, diclofenac, flurbiprofen and piroxicam; decongestants such as phenylephrine, naphazoline and tetrahydrozoline; miotics and anticholinesterases such as pilocarpine, salicylate, acetylcholine chloride, physostigmine, eserine, carbachol, diisopropyl fluorophosphate, phospholine iodide and demecarium bromide; mydriatics such as atropine sulfate, cyclopentolate, homatropine, scopolamine, tropicamide, eucatropine and hydroxyamphetamine; sypathomimetics such as epinephrine; antineoplastics such as carmustine, cisplatin and fluorouracil; immunological drugs such as vaccines and immune stimulants; hormonal agents such as estrogens, estradiol, progestational, progesterone, insulin, calcitonin, parathyroid hormone and peptide and vasopressin hypothalamus releasing factor; beta adrenergic blockers such as timolol maleate, levobunolol HCl and betaxolol HCl; growth factors such as epidermal growth factor, fibroblast growth factor, platelet derived growth factor, transforming growth factor beta, somatotropin and fibronectin; carbonic anhydrase inhibitors such as dichlorophenamide, acetazolamide and methazolamide and other drugs such as prostaglandins, antiprostaglandins and prostaglandin precursors; antioxidants, NMDA receptor antagonists, nootropics, anti-apoptotic agents, neurotrophins, neuroprotective agents, tyrosine kinase inhibitors (TKIs), dual leucine zipper kinase (DLK) inhibitors, cannabinoids, monoclonal antibodies, antibody fragments, other proteins, and gene therapy. Other therapeutic agents known to those skilled in the art which are capable of controlled, sustained release into the ear in the manner described herein are also suitable for use in accordance with embodiments of the devices described herein.

The therapeutic agent can include, but is not limited to sodium thiosulfate to protect against cisplatin-induced hearing loss; NMDA receptor antagonists for the treatment of tinnitus (AM-101; Auris Medical); AM-111 containing the synthetic peptide D-JNKI-1 (D-stereoisomer of c-Jun N-terminal Kinase Inhibitor 1; Auris Medical) for otoprotection in acute inner ear hearing loss; dexamethasone for the treatment of Meniere's Disease; D-methionine (Southern Illinois University) to protect against Noise-induced hearing loss; LY411575 (a selective gamma secretase inhibitor that blocks Notch activation); and NT-3 neurotrophic factor.

The therapeutic agent can include, but is not limited to local anesthetics for delivery into the ear canal including benzocaine, antipyrine, butamben, dibucaine, lidocaine, prilocaine, oxybuprocaine, pramoxine, proparacaine, proxymetacaine, and tetracaine.

Various pharmaceutically acceptable carriers for the therapeutic agents described herein can include such as, for example, solids such as starch, gelatin, sugars, natural gums such as acacia, sodium alginate and carboxymethyl cellulose; polymers such as silicone rubber; liquids such as sterile water, saline, dextrose, dextrose in water or saline; condensation products of castor oil and ethylene oxide, liquid glyceryl triester of a lower molecular weight fatty acid; lower alkanols; oils such as corn oil, peanut oil, sesame oil, castor oil, and the like, with emulsifiers such as mono- or di-glyceride of a fatty acid, or a phosphatide such as lecithin, polysorbate 80, and the like; glycols and polyalkylene glycols including P407 and other combinations of polyethylene glycol and polypropylene glycol; aqueous media in the presence of a suspending agent, for example, sodium carboxymethylcellulose, hyaluronic acid, sodium hyaluronate, sodium alginate, poly (vinyl pyrrolidone) and similar compounds, either alone, or with suitable dispensing agents such as lecithin, cyclodextrins, polyoxyethylene stearate and the like. The carrier may also contain adjuvants such as preserving, stabilizing, wetting, emulsifying agents or other related materials.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed. The claimed subject matter has been described in conjunction with the detailed description thereof, the foregoing description is intended to illustrate and not limit the scope of the claimed subject matter of the appended claims.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

What is claimed is:

1. A method of treating hearing loss of a patient, the method comprising:
   advancing, into an outer ear of the patient, a stabilizer insertion tool carrying a first stabilizer device defining a first working channel, the stabilizer insertion tool comprising a delivery shaft and a stylet with a beveled distal end that extends distally of the first stabilizer device;
   creating a first fenestration in a tympanic membrane of the patient using the beveled distal end of the stylet to penetrate the tympanic membrane while the stabilizer insertion tool is carrying the first stabilizer device;
   advancing the stabilizer insertion tool to implant the first stabilizer device in the first fenestration in the tympanic membrane;
   advancing, into an outer ear of the patient, the stabilizer insertion tool carrying a second stabilizer device defining a second working channel, the beveled distal end extending distally of the second stabilizer device;
   creating a second fenestration in the tympanic membrane of the patient using the beveled distal end of the stylet while the stabilizer insertion tool is carrying the second stabilizer device;
   advancing the stabilizer insertion tool to implant the second stabilizer device in the second fenestration in the tympanic membrane;
   advancing a first instrument through the first working channel while the first stabilizer device is implanted in the tympanic membrane; and
   advancing a second instrument through the second working channel while the second stabilizer device is implanted in the tympanic membrane.

2. The method of claim 1, wherein the first instrument comprises an endoscope.

3. The method of claim 2, wherein the second instrument comprises a microcannula.

4. The method of claim 3, further comprising injecting, via the microcannula, an inner ear therapeutic into a middle ear of the patient.

5. The method of claim 4, wherein the inner ear therapeutic comprises a biocompatible gel.

6. The method of claim 2, wherein the second instrument comprises a forceps.

* * * * *